United States Patent [19]

Farrar et al.

[11] Patent Number: 4,543,423

[45] Date of Patent: Sep. 24, 1985

[54] HYDRATION OF NITRILES

[75] Inventors: David Farrar; Peter Flesher, both of Bradford, England

[73] Assignee: Allied Colloids Limited, England

[21] Appl. No.: 437,385

[22] Filed: Oct. 28, 1982

[30] Foreign Application Priority Data

Oct. 29, 1981 [GB] United Kingdom ............... 8132660

[51] Int. Cl.[4] ........................................... C07C 102/08
[52] U.S. Cl. .................................... 564/128; 564/124; 564/126; 564/127
[58] Field of Search ............... 564/124, 126, 127, 128

[56] References Cited

U.S. PATENT DOCUMENTS

| 3,642,643 | 2/1972 | Habermann | 564/127 X |
| 3,642,894 | 2/1972 | Habermann et al. | 564/127 |
| 3,920,740 | 11/1975 | Svarz et al. | 564/127 |
| 3,994,973 | 11/1976 | Habermann et al. | 564/127 |
| 4,056,565 | 11/1977 | Matsuda | 564/127 |

*Primary Examiner*—Robert V. Hines
*Attorney, Agent, or Firm*—Lawrence Rosen

[57] ABSTRACT

A nitrile, such as acrylonitrile, is hydrated to the corresponding amide in the presence of a Raney copper catalyst that, before use in the reaction, is partially oxidized by contact with a controlled oxidizing system comprising oxygen, peroxide, iodate, chlorate, bromate or nitrate.

10 Claims, 1 Drawing Figure

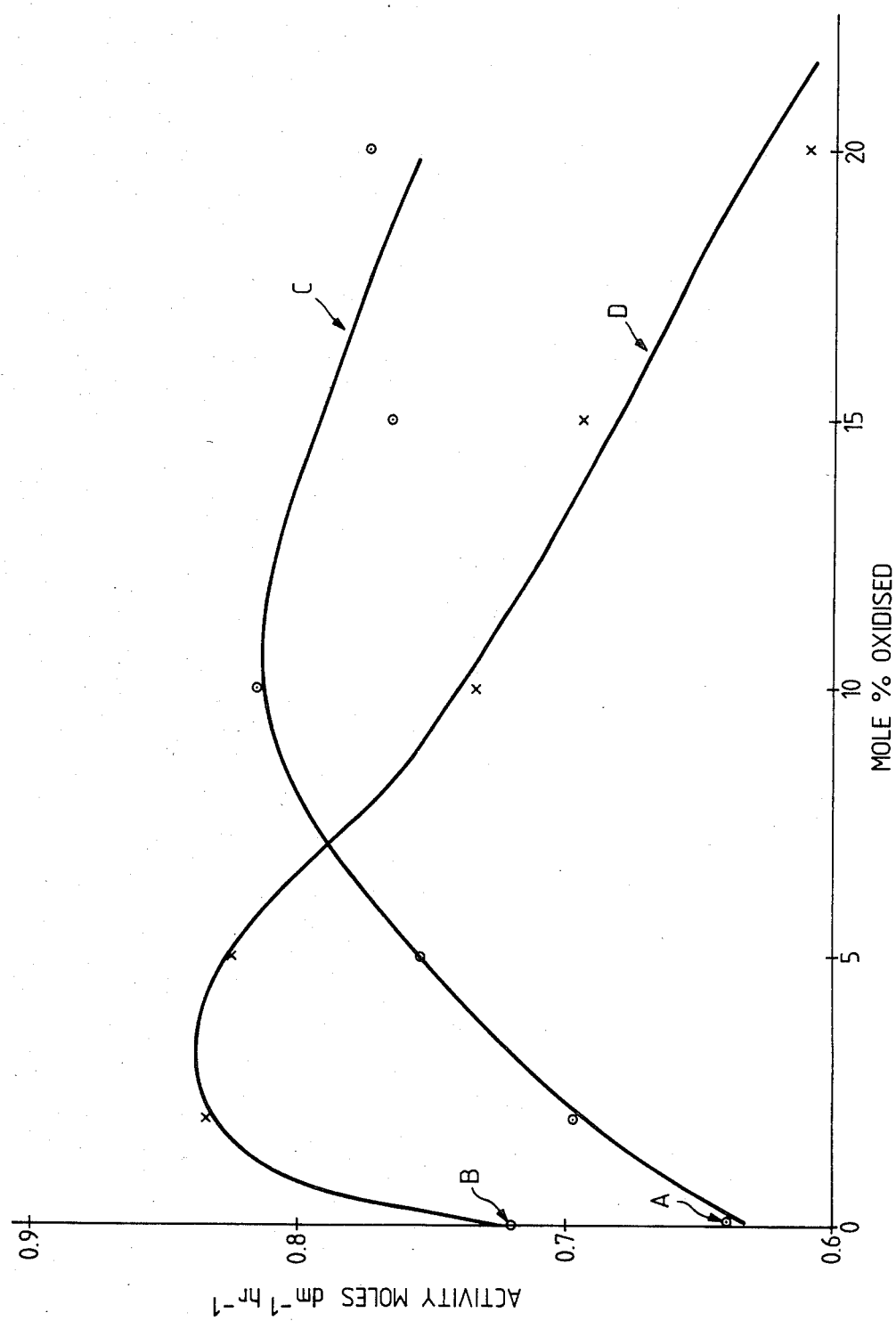

HYDRATION OF NITRILES

It is well known to use copper catalysts for use in the hydration of nitriles to amides, for example in the hydration of acrylonitrile to acrylamide.

In British Patent Specification No. 1324509 it is proposed to use a variety of metals, including forms of copper such as Raney copper, but copper oxide is specifically excluded.

In U.S. Pat. No. 3,631,104 it is stated that copper catalysts prepared by reducing copper oxide are preferred and that as more of the cupric oxide is reduced to cuprous oxide the activity of the catalyst increases. It is stated that preferred catalysts are those in which the copper content is essentially cuprous oxide containing a minor amount of copper metal.

In U.S. Pat. No. 3,642,894 it is proposed to use a reduced copper oxide catalyst. Cupric oxide may be reduced to either cuprous oxide or elemental copper while cuprous oxide may be at least partially reduced to elemental copper, and the catalyst generally contains a major amount of elemental copper and minor amounts of cuprous and cupric oxides. It is stated that the catalyst should be protected from oxygen after reduction and that contact of the catalyst with air or other oxygen containing gas should be avoided.

Complete reduction of a cuprous compound is proposed in U.S. Pat. No. 4,040,980.

In U.S. Pat. No. 3,766,088 it is proposed to use metallic copper catalysts including Raney copper and reduced copper and it is stated that the catalyst becomes deactivated during the hydration reaction and that this is caused, in part, by partial oxidation of the catalyst. Similarly, in U.S. Pat. No. 3,886,213 it is stated that the catalytic activity of reduced copper catalyst deteriorates after reduction and that this is due to oxidation of the catalyst. It is proposed that the freshly prepared catalyst should be treated in dilute nitrite solution but it is not clear what chemical effect this has.

The art therefore recognises that catalysts suitable for the reaction may be of Raney copper or may be made by reducing a copper oxide wholly or in part, and that oxidation of the reduced catalysts leads to deactivation.

In European Pat. No. 0037178 a process is described in which the activity of a copper containing catalyst useful in producing amides from nitriles by hydrolysis is maintained by utilising the catalyst as at least one electrode of an electrochemical reactor containing a solution comprising nitrile and water, and applying a direct current to the reactor at least intermittently as required to maintain the activity. In particular the current is applied to maintain what is described as a partial surface coverage having an average thickness 0.75 to 12.5 monolayers of ionic copper.

It appears that, in every instance, the required partial surface coverage is obtained as a result of reduction of oxidised copper, in all the examples by the reduction of oxidised Raney copper. In examples 1 to 8 reduction is by hydrogen (presumably to convert cupric oxide to cuprous oxide) and then by acidic hydrazene sulphate. In the other examples the initial reduction is by electrolysis. Although it is stated that the pretreatment and the maintenance electrolysis provides a partial surface coverage of 0.75 to 12.5 monolayers of ionic copper it is improbable that the surface does in fact consist, at any one point, of such monolayers over a Raney copper substrate. Since it is made by reduction of oxidised Raney copper it is very probable that there will be a tendency for metallic copper to be on the surface and for the ionic copper to be interspersed with the metallic copper or to be beneath the surface.

Irrespective of the precise mechanism, it is clear that the precise amount of ionic copper is regarded in European Specification No. 0037178 as being critical and it is difficult to regulate chemical reduction conditions to give the critical amount and it is difficult to operate, in practice, electrolysis reduction conditions. The normal process for hydration of a nitrile can comprise feeding granular catalyst to the reactor and relying upon the granules breaking down into powder as they become exhausted, so that the powdered spent catalyst is removed from the reactor with the reaction product. It is not easy to adapt such a process to include electrolysis of the catalyst granules.

It has therefore been our object to devise a simple way of improving the yield of the hydration reaction without having to change the standard operating conditions for the reaction.

In the invention a nitrile is hydrated to an amide in a reaction medium containing Raney copper catalyst and, before utilisation in the reaction medium, the catalyst is converted to a partially oxidised state by contact of Raney copper with a controlled oxidising system comprising oxygen, peroxide, iodate, chlorate, bromate or nitrate. Thus in the invention we start with Raney copper, that is to say copper which has been freshly made by leaching an alkali soluble metal from an alloy of that metal with copper, and which is wholly in the metallic, non-oxidised state, and then we partially oxidise it by one of the specified controlled oxidising systems. This results in a significant improvement in activity, compared to the unoxidised Raney copper.

The advantage is only obtained when one of the defined oxidising systems is used. For instance attempts to obtain the same effect using other oxidising agents that might be expected to work in a similar manner have failed. For instance advantageous improvement is not obtained when oxidation is attempted with permanganate, dichromate, bromine, iodine or hypochlorite.

It therefore seems that the specified oxidising agents are producing some unique effect that is concentrated solely at the surface of the Raney copper and that is not obtainable by other oxidising agents. Similarly, since it is apparently a truly surface effect, it inevitably is different from the depthwise effect which is obtained by the reduction process of European Specification No. 0037178. Additionally it is advantageous compared to that process since it involves a single, partial oxidation process by a simple chemical means compared to full oxidation and then partial reduction to a critical, and difficult to control, degree by electrolysis.

It is important in the invention that the catalyst is converted to only a partially oxidised state before utilisation in the reaction medium, and once the chosen degree of preoxidation has been achieved it is desirable to prevent substantial further oxidation. Normal precautions should be conducted to prevent further oxidation of the catalyst before use in the reaction medium and to prevent or minimise oxidation of the catalyst in the reaction medium. Thus any handling of the catalyst, before use in the reaction medium, should be under an inert atmosphere and the reaction medium should be deoxygenated, in the usual manner.

The controlled oxidising system generally comprises aerated water or a solution in substantially deaerated water of a peroxide, iodate, chlorate, bromate or nitrate. Solutions in solvents instead of water may be used, for instance alcohols.

The desired partially oxidised state is generally from 0.1 to 30%, preferably 0.5 to 20% and most preferably 1 to 15%. The precise chemical nature of the catalyst is not clear but it appears that it may be a mixture of copper and cupric oxide and by saying that the extent of preoxidation is 0.1 to 30% we mean that the amount of oxygen bound in the catalyst is equivalent to the catalyst consisting of 0.1 to 30% cupric oxide with the balance being metallic copper.

It seems that when Raney copper is exposed to the defined controlled oxidation systems some oxidation occurs very rapidly and any further oxidation then occurs more slowly. The desired partial degree of oxidation appears to correspond approximately with the amount of oxidation at the end of the first, very fast, stage of oxidation. Thus, when Raney copper is immersed in oxygenated water a suitable (and often the optimum) degree of pre-oxidation coincides with the point at which the absorbtion rate of oxygen changes from a rapid initial rate to a slower rate. It is therefore probable that the effective preoxidation results in modification of the surface layer only and that penetration of oxygen into the interior has a detrimental effect on catalyst efficiency. This is in contrast to the process of European Specification No. 0037178 where oxygen is inevitably present in the interior of the catalyst.

The contact with the controlled oxidising system may be effected over a relatively short time, for instance 10 minutes to 3 hours at ambient temperatures, for instance 10° to 35° C. However longer durations, e.g. up to 8 hours or more, may be permissible at such temperatures since further reaction is very slow. Higher temperatures, e.g. up to 100° C., may be permissible provided the duration of contact is short. Contact may be achieved by stirring the catalyst with the aerated water or other solution at the chosen temperature. When the oxidising system is a solution in substantially deaerated water of a peroxide, iodate, chlorate, bromate or nitrate the concentration of the oxidising ion is generally between 100 and 4000 ppm. Peroxide may be introduced as hydrogen peroxide and preferably is present in a concentration of 500 to 1500 ppm. Iodate, chlorate, bromate or nitrate may be introduced as salts with alkali metals, such as potassium or sodium. Preferred concentration of iodate is from 1000 to 4000 ppm. Preferred concentration of chlorate is from 500 to 3000 ppm. The preferred concentration of bromate is from 500 to 3500 ppm and the preferred concentration of nitrate is from 500 to 3000 ppm.

The optimum degree of oxidation in any particular process depends in part upon whether or not the reaction medium includes a promotor for the copper catalyst. Promotors for copper catalysts in the hydration of a nitrile to an amide are known and such promotors can be used in the invention. The promotors generally are copper salts, for instance cupric sulphate, nitrate or halide or a copper salt with a fatty acid, or the promotor may be a nitrate, for instance aluminium nitrate. The amount of promotor normally is from 5 to 400 ppm, calculated as metal, based on the water and nitrile in the reaction mixture. Best results are generally obtained with 150 to 350 ppm of a copper salt, measured as copper. When the catalyst is promoted the optimum degree of partial oxidation is generally from 0.5 to 10%. When the catalyst is unpromoted the optimum amount of partial oxidation is generally from 5 to 15%, most preferably around 10%.

If the amount of preoxidation or other oxidation of the catalyst is too high, then the catalyst efficiency may be reduced and the formation of cyanohydrins and other by-products may become significant. However, at the preferred values the production of these by-products is insignificant.

The Raney copper is generally made by alkali (usually sodium hydroxide) leaching of alloys such as CuMg, CuAl and CuZn, but best results are obtained in the invention when the Raney copper is derived from CuAl alloy. It should be handled under non-oxidising conditions, in conventional manner, so as to prevent oxidation of it before the controlled partial oxidation of the invention.

The controlled partial oxidation is effected before the catalyst is used in the reaction medium for the hydration of nitrile to amide. It may be effected in the reaction vessel in which the hydration is to be conducted, for instance before introducing the nitrile into the reaction vessel, but generally it is effected in a separate vessel and the partially oxidised catalyst is introduced into the hydration reaction vessel while preventing further oxidation of it.

The hydration may then be conducted in conventional manner, the reaction medium consisting generally only of the nitrile, deaerated water, catalyst, promotor if present, and the products of the reaction. The hydration is normally conducted at temperatures of from 50° to 200° C. The reaction medium usually includes at least 0.5 moles, and usually at least 1 mole, water per mole nitrile. The nitriles that may be hydrated in the invention are those of the formula R(CN)x where x is 1–4 and R is $C_{1-8}$ alkyl, $C_{2-8}$ alkenyl or $C_{6-10}$ aryl. Acrylonitrile is the preferred nitrile.

The catalyst is generally introduced into the reaction vessel in the form of granules, for instance having a particle size of from 30 to 300 microns, generally 50 to 100 microns. The promotor may be introduced as an aqueous solution. The hydration may be carried out continuously or batchwise, generally with continuous or intermittent feed of nitrile and continuous or intermittent withdrawal of reaction product.

In a continuous process the catalyst may be continuously or intermittently fed to the reaction vessel. As the catalyst becomes exhausted the granules break down to form powder and this powder is carried from the reaction vessel by the outflowing reaction product.

In a batchwise process, the process is terminated when the catalyst is exhausted and the exhausted catalyst is discharged from the reaction vessel. All the catalyst required for the process may be charged to the vessel at the start of the batch, or some may be added during the process. The duration of the batch may typically be 4 to 12 hours.

The invention includes not only the described process but also the partially oxidised catalyst and processes of making it.

The following are examples of the invention.

EXAMPLE 1

A Raney copper catalyst was prepared using the following recipe.

Wt. of Cu:Al alloy = 30 g
Addition time = 40 ± 5 mins
Wt. of 25% NaOH = 178 g
Reaction temperature = 50°–60° C.

Period of Ageing = 60 mins

The catalyst was washed by decantation using 200 ml of aliquots of deoxygenated, deionised water and stirred for 5 minutes until the pH of the washings was less than 10. It is essential to have truly deoxygenated conditions, i.e. it is necessary to purge the washing-flask continuously with a rapid stream of nitrogen and to minimise the washing period.

Activity tests were performed in a 250 ml 3-necked flask fitted with stirrer, condenser, $N_2$ inlet and serum cap. The weight of catalyst was 2.5 g, weight of water 52.5 g, weight of acrylonitrile 10.5 g. All solutions were deoxygenated prior to use. Samples were withdrawn through the serum-cap, filtered and analysed by GLC. The activity value of the catalyst was taken as the molarity of the acrylamide solution after a reaction time of one hour at 74° C.

Four tests were conducted. In test A the described Raney copper catalyst was used, without preoxidation, without promotor. The activity was 0.64. In test B the same catalyst was used but in the presence of copper nitrate in an amount of 250 ppm $Cu^{++}$ based on water and acrylonitrile, as promotor. The activity was 0.72. In test C the catalyst was partially oxidised and was used without promotor (as in test A) and in test D it was partially oxidised and used with the same promotor as in test B. The partial oxidation in each of tests C and D was effected by placing the catalyst in deionised, deoxygenated water in a flask held 25° C. and oxygen was displaced into the flask and the reduction in volume as the reaction proceeded over a period of 3 hours to 20% oxidation, as CuO. The degree of oxidation was calculated by pH titration.

The activity of the catalyst was recorded at varying levels of oxidation and the results are shown in the accompanying graphs. These demonstrate clearly the very advantageous effect of preoxidation, with best results being achieved in the particular conditions in the example at about 3% oxidation for the promoted catalyst (test D) and 10% oxidation for the non-promoted catalyst (test C).

EXAMPLE 2

Raney copper catalyst was prepared as in Example 1. Samples of the catalyst were contacted with aqueous solutions of, respectively, potassium bromate, potassium chlorate, potassium nitrate, potassium iodate, hydrogen peroxide, potassium permanganate, potassium dichromate, sodium hypochlorite, chlorine and bromine, at varying concentrations but at a temperature of 80° C. for 2 hours with continuous nitrogen flushing. The resultant catalysts, and untreated catalysts, were then subjected to activity tests as described in Example 1 and the following results were obtained.

| Pre-Treatment | Activity (moles dm$^{-3}$ hr$^{-1}$) |
| --- | --- |
| 1000 ppm $BrO_3^-$ | 0.89 |
| 2000 ppm $ClO_3^-$ | 0.77 |
| 1500 ppm $ClO_3^-$ | 0.80 |
| 1000 ppm $ClO_3^-$ | 0.88 |
| 500 ppm $ClO_3^-$ | 0.72 |
| 250 ppm $ClO_3^-$ | 0.74 |
| None | 0.65 |
| 350 ppm $NO_3^-$ | 0.96 |
| None | 0.71 |
| None | 0.52 |
| 1000 ppm $H_2O_2$ | 0.84 |
| None | 0.57 |
| 1000 ppm $MnO_4^-$ | 0.52 |

-continued

| Pre-Treatment | Activity (moles dm$^{-3}$ hr$^{-1}$) |
| --- | --- |
| 1000 ppm $CrO_7^-$ | 0.55 |
| 1000 ppm $ClO^-$ | 0.56 |
| 1000 ppm $Cl_2$ | 0.07 |
| 1000 ppm $Br_2$ | 0.05 |

EXAMPLE 3

A Raney copper catalyst is made as in Example 1 and is then stirred in a deaerated aqueous solution at 80° C. containing 1000 ppm $BrO_3^-$ for 2 hours with continuous nitrogen flushing. The catalyst is in granular form, having an average particle size of about 74 μm.

A reaction vessel that is maintained at 100° C. is charged with 1000 parts of the described catalyst. Acrylonitrile and deaerated water are continuously introduced into the vessel at 1000 parts per hour and 342 parts per hour respectively. Reaction product is continuously taken from the top of the vessel. The product consists of 31.5 acrylamide and 2% acrylonitrile after the system has reached steady state. The process runs for 8 hours and the reactor is then emptied.

We claim:

1. In a process wherein a nitrile is hydrated to an amide in a deoxygenated reaction medium containing Raney copper catalyst; the improvement which comprises increasing catalyst activity by preoxidising the Raney copper catalyst, prior to contact with the reaction medium, with a controlled oxidising system comprising an oxidant selected from the group consisting of oxygen, peroxide, iodate, chlorate, bromate and nitrate to obtain Raney copper in a partially oxidised state ranging from about 0.1 to 30%, and then contacting the preoxidised Raney copper catalyst with the deoxygenated reaction medium.

2. In the process according to claim 1 in which the controlled oxidising system is selected from aerated water and solutions in a solvent selected from substantially deaerated water and alcohol of an oxidant selected from peroxide, iodate, chlorate, bromate and nitrate.

3. In the process according to claim 1 in which the controlled oxidising system is selected from aerated water and solutions in deaerated water of from 100 to 4000 ppm of an oxidant selected from peroxide, iodate, chlorate, bromate and nitrate.

4. In the process according to claim 1 in which the partially oxidised state of the catalyst is 0.5 to 20% oxidation.

5. In the process according to claim 1 conducted in the absence of a promotor and the partially oxidized state of the catalyst is 5 to 15% oxidation.

6. In the process according to claim 1 conducted in presence of a promotor.

7. In the process according to claim 6 in which the promotor is a cupric salt or a nitrate.

8. In the process according to claim 6 in which the partially oxidised state of the catalyst is 0.5 to 10% oxidation.

9. In the process according to claim 1 in which the hydration is conducted continuously or batchwise in a reaction vessel with continuous or intermittent feed of the nitrile and water to a reaction vessel and with continuous, intermittent or batchwise feed of granular, preoxidised Raney copper catalyst into the vessel and in which spent catalyst is removed continuously or intermittently as powder with reaction product or is discharged from the vessel at the end of a batch.

10. In the process according to claim 1 in which the nitrile is acrylonitrile and the amide is acrylamide.

* * * * *